US009849075B2

(12) United States Patent
Tokunaga et al.

(10) Patent No.: US 9,849,075 B2
(45) Date of Patent: Dec. 26, 2017

(54) GEL HAIR COSMETIC

(71) Applicant: KAO CORPORATION, Chuo-ku (JP)

(72) Inventors: Shinichi Tokunaga, Sumida-ku (JP);
Hiroto Tanamachi, Yachiyo (JP);
Ryosuke Suzuki, Tokorozawa (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/655,935

(22) PCT Filed: Dec. 12, 2013

(86) PCT No.: PCT/JP2013/083346
§ 371 (c)(1),
(2) Date: Jun. 26, 2015

(87) PCT Pub. No.: WO2014/103739
PCT Pub. Date: Jul. 3, 2014

(65) Prior Publication Data
US 2016/0000690 A1 Jan. 7, 2016

(30) Foreign Application Priority Data

Dec. 26, 2012 (JP) ................................. 2012-283746

(51) Int. Cl.
A61K 8/84 (2006.01)
A61K 8/34 (2006.01)
A61K 8/41 (2006.01)
A61Q 5/12 (2006.01)
A61K 8/04 (2006.01)
A61Q 5/06 (2006.01)

(52) U.S. Cl.
CPC ............... *A61K 8/84* (2013.01); *A61K 8/042* (2013.01); *A61K 8/34* (2013.01); *A61K 8/41* (2013.01); *A61Q 5/06* (2013.01); *A61Q 5/12* (2013.01); *A61K 2800/10* (2013.01)

(58) Field of Classification Search
CPC ...... A61K 2800/10; A61K 8/042; A61K 8/34; A61K 8/41; A61K 8/84; A61Q 5/06; A61Q 5/12
See application file for complete search history.

(56) References Cited

U.S. PATENT DOCUMENTS

| 3,980,091 | A | 9/1976 | Dasher et al. | |
|---|---|---|---|---|
| 6,399,741 | B1 | 6/2002 | Fry et al. | |
| 6,579,846 | B1* | 6/2003 | Zirnstein | C08G 73/0233 510/130 |
| 7,026,435 | B2 | 4/2006 | Fry et al. | |
| 2002/0146379 | A1* | 10/2002 | Shefer | A61K 8/0283 424/70.12 |
| 2003/0190335 | A1 | 10/2003 | Boussouira et al. | |
| 2004/0234485 | A1* | 11/2004 | Maubru | A61K 8/23 424/70.16 |
| 2006/0182702 | A1* | 8/2006 | Lazzeri | A61K 8/342 424/70.13 |
| 2009/0169502 | A1 | 7/2009 | Quadir | |
| 2013/0303725 | A1* | 11/2013 | Dobrawa | C11D 3/3723 528/405 |
| 2014/0199253 | A1 | 7/2014 | Hindley et al. | |

FOREIGN PATENT DOCUMENTS

| JP | 53 38636 | 4/1978 |
|---|---|---|
| JP | 63-165306 | 7/1988 |
| JP | 1 190619 | 7/1989 |
| JP | 6 172522 | 6/1994 |
| JP | 6-299141 A | 10/1994 |
| JP | 7 188698 | 7/1995 |
| JP | 8 217643 | 8/1996 |
| JP | 9 157113 | 6/1997 |

(Continued)

OTHER PUBLICATIONS

Technical information for Lupasol types. The chemical company BASF. Care Chemicals & Formulations. 2010, pp. 1-10.*
International Preliminary Report of Patentability and Written Opinion dated Jul. 9, 2015 in PCT/JP2013/083346 (English translation only).
Tanamachi, H., et al., "Deposition of 18-MEA onto alkaline-color-treated weathered hair to form a persistent hydrophobicity", J. Cosmet. Sci., vol. 60, (Jan./Feb. 2009), pp. 31-44.
Tanamachi, H., et al., "18-MEA and hair appearance", J.Cosmet. Sci., vol. 61, (Mar./Apr. 2010), pp. 147-160.

(Continued)

*Primary Examiner* — Robert A Wax
*Assistant Examiner* — Olga V Tcherkasskaya
(74) *Attorney, Agent, or Firm* — Oblon, McClelland, Maier & Neustadt, L.L.P.

(57) ABSTRACT

The invention provides a gel-form hair cosmetic composition, which contains components (a) to (c) emulsified in an aqueous component, and which exhibits an endothermic peak temperature of from 40° C. to 75° C. as measured through DSC, wherein the components are (a) a polyalkyleneimine derivative or a salt thereof, the polyalkyleneimine derivative being formed of a polyalkyleneimine having a weight average molecular weight of from 3,300 to 50,000, in which one of the substituents of $R^1$—CO—, $R^2$—$(CH_2)_n$—CHX—$CH_2$—, and $R^3$—NH—CO— [$R^1$ is H, alkyl, alkenyl, or the like; $R^2$ is H, alkyl, alkoxy, alkenyl or the like; n is 0 or 1; X is H or OH; $R^3$ is H, alkyl, or alkenyl; at least one of $R^1$ to $R^3$ has 13 or more carbon atoms; and the entirety of $R^1$, $R^2$, and $R^3$ has an average number of carbon atoms of 9 or more and a linear group content of 30 mol % or more] is bonded to 40 mol % or more of the nitrogen atoms of the polyalkyleneimine; (b) a C12 to C28 saturated aliphatic alcohol; and (c) a cationic surfactant.

20 Claims, No Drawings

(56) References Cited

FOREIGN PATENT DOCUMENTS

| JP | 2000 178145 | 6/2000 |
|---|---|---|
| JP | 2002 308738 | 10/2002 |
| JP | 2006-219493 A | 8/2006 |
| JP | 2009-161762 A | 7/2009 |
| JP | 2010 77061 | 4/2010 |
| JP | 2012 236804 | 12/2012 |
| JP | 2013 32326 | 2/2013 |
| JP | 2013 216620 | 10/2013 |
| JP | 2014 141485 | 8/2014 |
| WO | WO 98/04233 A1 | 2/1998 |

OTHER PUBLICATIONS

Yasuda, M., "Hand Combing Sensation and Stiffness of Hair, and Science of Hair Surface", Journal of Hair Science, vol. 95, (2004), pp. 7-12, (with computer generated English translation).
Tanaka, N., "Natural Intention in hair care products", Fragrance Journal, No. 6, (1986), pp. 44-52.
International Search Report dated Mar. 11, 2014 in PCT/JP2013/083346 Filed Dec. 12, 2013.
Extended European Search Report dated Oct. 4, 2016 in Patent Application No. 13867623.4.

\* cited by examiner

GEL HAIR COSMETIC

CROSS REFERENCE TO RELATED APPLICATION

This application is a National Stage entry under 35 USC 371 of PCT/JP2013/083346, filed on Dec. 12, 2013, and claims priority to Japanese Patent Application No. 2012-283746, filed on Dec. 26, 2012.

FIELD OF THE INVENTION

The present invention relates to a gel-form hair cosmetic composition containing a high-molecular-weight polyalkyleneimine derivative or a salt thereof, the polyalkyleneimine derivative having substituents including a long-chain alkyl group with high substitution degree.

BACKGROUND OF THE INVENTION

In recent years, hair damage, particularly damage of hair end portions, has been more grave due to hair setting treatments with heat, such as a hair treatment with a hair iron, a drier, and the like, which are popular among young women, in addition to hair setting treatments with chemicals, such as hair coloring and permanent wave treatment. It is reported that hair damage involves loss of 18-MEA (18-methyleicosanoic acid), which is a fatty acid covering hair surfaces, whereby the hair surfaces are hydrophilicized, and hair surface friction increases (see Non-Patent Documents 1 to 3).

When having received repeated damage, hair cosmetic users complain of the resulting conditions such as entanglement of hair ends during styling, failure to make a hair style as desired, and poor hand combing performance. Thus, there is demand for a technique of restoring hydrophobicity intrinsic to healthy hair and low friction between hair filaments (hereinafter referred to simply as "hair friction") in a wet state, using a material which absorbs on damaged hair ends. Regarding such techniques, there have been proposed a hair cosmetic composition containing an amino-modified silicone, a cationic surfactant, and an amphoteric polymer (JPH01-190619); a shampoo composition containing a surfactant, an amino-modified silicone, and a water-soluble polymer (JPH08-217643); a hair cosmetic composition containing an amino-group-bearing organopolysiloxane formed through reaction between a poly-functional amine compound and an organosiloxane having an epoxy group at one or both ends (JP2002-308738), and a similar composition.

CITATION LIST

Non-Patent Documents

Non-Patent Document 1: Hiroto Tanamachi et al. (seven other co-authors), "Deposition of 18-MEA onto Alkaline-Color-Treated Weathered Hair to Form a Persistent Hydrophobicity," Journal of Cosmetic Science, 60, 31-44 (2009)

Non-Patent Document 2: Hiroto Tanamachi et al. (four other co-authors), "18-MEA and Hair Appearance," Journal of Cosmetic Science, 61, 147-160 (2010)

Non-Patent Document 3: Masaaki Yasuda, "Hand Combing Sensation and Stiffness of Hair, and Science of Hair Surface," Journal of Hair Science, 95, 7-12 (2004)

SUMMARY OF THE INVENTION

The present invention provides a gel-form hair cosmetic composition, which is a gel-form aqueous composition containing the following components (a), (b), and (c) emulsified in an aqueous component, which gel exhibits an endothermic peak temperature of 40° C. to 75° C. as measured by means of a differential scanning calorimeter (DSC).

(a) A polyalkyleneimine derivative or a salt thereof, the polyalkyleneimine derivative being formed of a polyalkyleneimine having a weight average molecular weight of 3,300 to 50,000, in which at least one of the substituents represented by any of formulas (I), (II), and (III) is bonded to 40 mol % or more of the nitrogen atoms of the polyalkyleneimine, the formulas being:

$R^1$—CO—  (I)

$R^2$—$(CH_2)_n$—CHX—$CH_2$—  (II)

$R^3$—NH—CO—  (III)

[wherein, in formula (I), $R^1$ represents a group selected from the group consisting of a hydrogen atom, and an alkyl group, an alkenyl group, and a hydroxyalkyl group, in the form of a linear chain group or a branched chain group;

in formula (II), $R^2$ represents a group selected from the group consisting of a hydrogen atom, and an alkyl group, an alkoxy group, an alkenyl group, and an alkenyloxy group, in the form of a linear chain group or a branched chain group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;

in formula (III), $R^3$ represents a group selected from the group consisting of a hydrogen atom, and an alkyl group and an alkenyl group, in the form of a linear chain group or a branched chain group; and $R^1$, $R^2$, and $R^3$ may be identical to or different from one another, and at least one of $R^1$, $R^2$, and $R^3$ is a group having 13 or more carbon atoms; the entirety of $R^1$, $R^2$, and $R^3$ has an average number of carbon atoms of 9 or more; and the entirety of $R^1$, $R^2$, and $R^3$ has a linear group content of 30 mol % or more];

(b) a C12 to C28 saturated aliphatic alcohol; and (c) a cationic surfactant.

The present invention also provides a method for modifying hair, the method comprising applying the aforementioned gel-form hair cosmetic composition to hair, and spreading the composition over the hair.

DETAILED DESCRIPTION OF THE INVENTION

When a conventional conditioning technique is employed, generally, an applied liquid oil is not readily adsorbed in the hair surface which has been damaged to become hydrophilic, and thus the hair surface is non-uniformly coated with the oily liquid. In such a case, the intrinsic hydrophobicity of hair is thought to be unrecovered. Also, when the liquid content is elevated in order to cause the liquid oil to be adsorbed on the entire hair surface, a coarse hair sensation of users problematically increases in a wet state.

Thus, the present invention is to provide a hair cosmetic composition which can realize uniform adsorption of a conditioning base on the hair end surface that has been damaged to have hydrophilicity and which can restore the hydrophobicity intrinsic to healthy hair and low hair friction in a wet state.

The present inventors found that the aforementioned object can be attained by a gel-form hair cosmetic composition containing a polyalkyleneimine derivative or a salt thereof, an aliphatic alcohol, and a cationic surfactant, which have specific characteristics.

[Component (a): Polyalkyleneimine Derivative or a Salt Thereof]

Component (a) is a polyalkyleneimine derivative or a salt thereof, the derivative formed of a polyalkyleneimine having a weight average molecular weight of 3,300 to 50,000, in which at least one of the substituents represented by any of formulas (I), (II), and (III) is bonded to 40 mol % or more of the nitrogen atoms of the polyalkyleneimine, the formulas being:

$$R^1-CO- \quad (I)$$

$$R^2-(CH_2)_n-CHX-CH_2- \quad (II)$$

$$R^3-NH-CO- \quad (III)$$

[wherein, in formula (I), $R^1$ represents a group selected from the group consisting of a hydrogen atom, and an alkyl group, an alkenyl group, and a hydroxyalkyl group, in the form of a linear chain group or a branched chain group;

in formula (II), $R^2$ represents a group selected from the group consisting of a hydrogen atom, and an alkyl group, an alkoxy group, an alkenyl group, and an alkenyloxy group, in the form of a linear chain group or a branched chain group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;

in formula (III), $R^3$ represents a group selected from the group consisting a hydrogen atom, and an alkyl group and an alkenyl group, in the form of a linear chain group or a branched chain group; and $R^1$, $R^2$, and $R^3$ may be identical to or different from one another; the entirety of $R^1$, $R^2$, and $R^3$ has an average number of carbon atoms of 9 or more; and the entirety of $R^1$, $R^2$, and $R^3$ has a linear group content of 30 mol % or more].

The polyalkyleneimine, which is a source of component (a), is preferably a polyethyleneimine or a polypropyleneimine, with a polyethyleneimine having a branch structure being particularly preferred. The tertiary amino group content of the polyethyleneimine, based on the total amount of nitrogen atoms, is preferably about 10 mol % or more, more preferably 20 mol % or more, still more preferably 25 mol % or more, and preferably 40 mol % or less, more preferably 35 mol % or less. The weight average molecular weight (as determined through gel permeation chromatography (GPC) and reduced to pullulan) of the polyalkyleneimine is 3,300 or more, preferably 4,000 or more, more preferably 4,500 or more, still more preferably 5,000 or more, from the viewpoints of enhancing adsorption of component (a) on damaged portions of hair and facilitating provision of a conformation for realizing high alkyl group packing, to thereby restore hydrophobicity and low hair friction in a wet state. From the viewpoint of the effect of forming a stable gel-form composition, the molecular weight is 50,000 or less, preferably 40,000 or less, more preferably 30,000 or less, still more preferably 20,000 or less, yet more preferably 10,000 or less. Meanwhile, the weight average molecular weight of polyalkyleneimine determined through the method disclosed in the Examples of the present specification differs from a nominal molecular weight given by the manufacturer of the polyalkyleneimine. Specifically, the determined value is from about 1.5 to about 5 times the nominal value. Thus, in the present invention, the weight average molecular weight determined through the method disclosed in the Examples of the present specification is employed. Polyethyleneimine may be produced through a method generally known in the art, and such products are commercially available. Examples of commercial products of polyethyleneimine include EPOMIN (product of Nippon Shokuba, Co., Ltd.) and Lupasol (BASF).

The weight average molecular weight (as determined through gel permeation chromatography (GPC) and reduced to polystyrene) of the polyalkyleneimine derivative or a salt thereof—component (a)—is preferably 2,500 or more, more preferably 3,000 or more, still more preferably 3,500 or more, and preferably 50,000 or less, more preferably 40,000 or less, still more preferably 20,000 or less, yet more preferably 10,000 or less, from the viewpoints of enhancing adsorption of component (a) on damaged portions of hair and facilitating provision of a conformation for realizing high alkyl group packing, to thereby restore hydrophobicity and low hair friction in a wet state. The weight average molecular weight of the polyalkyleneimine derivative or a salt thereof—component (a)—employed in the present specification is also a value determined through the method disclosed in the Examples.

To polyalkyleneimine, the substituent represented by formula (I) may be added through a known method. In one procedure, a polyalkyleneimine is reacted with a fatty acid, a fatty acid ester, a fatty acid halide, or the like. When two or more species of the fatty acid, the fatty acid ester, the fatty acid halide, or the like are reacted, two or more substituents having different structures can be added. Such a synthesis method is disclosed in, for example, JPH09-157113 A.

To polyalkyleneimine, the substituent represented by formula (II) may be added through a known method. In one procedure, a polyalkyleneimine is reacted with an alkyl halide, an epoxyalkane, a glycidyl ether having an alkyl group or an alkenyl group, or the like. When two or more species of the alkyl halide, the epoxyalkane, the glycidyl ether having an alkyl group or an alkenyl group, or the like are reacted, two or more substituents having different structures can be added. Such a synthesis method is disclosed in, for example, JPH06-299141A or JP2009-161762A.

To polyalkyleneimine, the substituent represented by formula (III) may be added through a known method. In one procedure, a polyalkyleneimine is reacted with an isocyanate having an alkyl group or an alkenyl group, or the like. When two or more species of the isocyanate having an alkyl group or an alkenyl group, or the like are reacted, two or more substituents having different structures can be added. Such a synthesis method is disclosed in, for example, JPS40-17661B.

In the polyalkyleneimine derivative or a salt thereof (component (a)), the ratio of the amount of the substituent represented by formula (I), (II), or (III) to the total amount of the substituents represented by any of formulas (I), (II), and (III) is not limited. However, the ratio of the substituent represented by formula (I) is preferably form 20 mol % or more to 100 mol % or less, more preferably from 40 mol % or more to 100 mol % or less, still more preferably from 60 mol % or more to 100 mol % or less, yet more preferably from 80 mol % or more to 100 mol % or less. The total ratio of the substituents represented by formulas (II) and (III) is preferably from 0 mol % or more to 80 mol % or less, more preferably from 0 mol % or more to 60 mol % or less, still more preferably from 0 mol % or more to 40 mol % or less, yet more preferably from 0 mol % or more to 20 mol % or less.

In the polyalkyleneimine derivative or a salt thereof (component (a)), the ratio of the number of nitrogen atoms of the polyalkyleneimine, which atoms are bonded to a substituent represented by any of formulas (I), (II), and (III), to the number of all nitrogen atoms; i.e., the substitution ratio, is 40 mol % or more among the nitrogen atoms of the polyalkyleneimine, preferably 45 mol % or more, more preferably 50 mol % or more, from the viewpoint of the effect of hydrophobicizing the hair surface. The component (a) substitution ratio may be determined by, for example, calculating the ratio of the integrated area of the peak attributed to the polyalkyleneimine skeleton to that of the peak attributed to the relevant substituent, in measurement of an NMR spectrum of the produced polyalkyleneimine derivative or a salt thereof.

In formulas (I), (II), and (III), the alkyl group in $R^1$, $R^2$, or $R^3$ may be linear or branched. The number of carbon atoms of the alkyl group is preferably 1 or more, more preferably 2 or more, still more preferably 13 or more, yet more preferably 14 or more, and preferably 22 or less, more preferably 21 or less, still more preferably 18 or less, yet more preferably 17 or less, from the viewpoint of the effect of hydrophobicizing the hair surface. The branch structure is preferably a methyl branch or an ethyl branch, with a methyl branch being more preferred. Specific examples of the alkyl group include myristyl, pentadecyl, cetyl, heptadecyl, stearyl, isostearyl, nonadecyl, eicosyl, behenyl, 14-methylhexadecyl, 16-methyloctadecyl, 18-methylnonadecyl, and 18-methyleicosyl.

In formulas (I), (II), and (III), the alkenyl group in $R^1$, $R^2$, or $R^3$ may have one or more unsaturated bonds, and may be linear or branched. From the viewpoint of the effect of enhancing hydrophobicity, the number of carbon atoms of the alkenyl group is preferably 2 or more, more preferably 13 or more, still more preferably 14 or more, and preferably 22 or less, more preferably 21 or less, still more preferably 18 or less, yet more preferably 17 or less. From the viewpoint of the effect of reducing the friction of the hair surface, the branch structure is preferably a methyl branch or an ethyl branch, with a methyl branch being more preferred. Specific examples of the alkenyl group include tetradecenyl, pentadecenyl, hexadecenyl, heptadecenyl, octadecenyl, nonadecenyl, linolyl, linolenyl, and elaeostearyl.

In formula (I), the hydroxyalkyl group in $R^1$ may be linear or branched and preferably has one or two hydroxyl groups. The number of carbon atoms of the hydroxyalkyl group is preferably 1 or more, more preferably 2 or more, still more preferably 13 or more, yet more preferably 14 or more, and preferably 22 or less, more preferably 21 or less, still more preferably 18 or less, yet more preferably 17 or less. The branch structure is preferably a methyl branch or an ethyl branch, with a methyl branch being more preferred. Specific examples of the hydroxyalkyl group include 11-hydroxyheptadecyl, 8,9-bishydroxyheptadecyl, 3-hydroxyheptadecyl, 5-hydroxyeicosyl, and 12-hydroxystearyl.

In formula (II), the alkoxy group in $R^2$ may be linear or branched. From the viewpoint of the effect of enhancing hydrophobicity, the number of carbon atoms of the alkoxy group is preferably 1 or more, more preferably 2 or more, still more preferably 13 or more, yet more preferably 14 or more, and preferably 22 or less, more preferably 21 or less, still more preferably 18 or less, yet more preferably 17 or less. From the viewpoint of the effect of reducing the friction of the hair surface, the branch structure is preferably a methyl branch or an ethyl branch, with a methyl branch being more preferred. Specific examples of the alkoxy group include myristyloxy, pentadecyloxy, cetyloxy, heptadecyloxy, stearyloxy, 16-methyloctadecyloxy, 18-methylnonadecyloxy, and 18-methyleicosyloxy.

In formula (II), the alkenyloxy group in $R^2$ may be linear or branched. From the viewpoint of the effect of enhancing hydrophobicity, the number of carbon atoms of the alkenyloxy group is preferably 2 or more, more preferably 13 or more, still more preferably 14 or more, and preferably 22 or more, more preferably 21 or less, still more preferably 18 or less, yet more preferably 17 or less. From the viewpoint of the effect of reducing the friction of the hair surface, the branch structure is preferably a methyl branch or an ethyl branch, with a methyl branch being more preferred. Specific examples of the alkenyloxy group include tetradecenyloxy, pentadecenyloxy, hexadecenyloxy, heptadecenyloxy, octadecenyloxy, nonadecenyloxy, linolyloxy, linolenyloxy, and elaeostearyloxy.

$R^1$, $R^2$, and $R^3$ in formula (I), (II), and (III) may be identical to or different from one another. A plurality of $R^1$s, a plurality of $R^2$s, and a plurality of $R^3$s may also be identical to or different from one another. From the viewpoint of the effect of restoring hydrophobicity and low hair friction in a wet state, the entirety of $R^1$, $R^2$, and $R^3$ preferably has an average number of carbon atoms of 9 or more, more preferably 12 or more. Among $R^1$, $R^2$, and $R^3$ in all the substituents, at least one group has a number of carbon atoms of 13 or more. The ≥13C group content is preferably 50 mol % or more, more preferably 70 mol % or more. From the viewpoint of the effect of restoring the hydrophobicity of the hair surface, the entirety of $R^1$, $R^2$, and $R^3$ preferably has a linear structure content of 30 mol % or more, more preferably 40 mol % or more. From the viewpoint of the effect of restoring low friction in a wet hair state, the linear structure content is preferably 90 mol % or less, more preferably 80 mol % or less. From the viewpoint of the effect of restoring low friction in a wet hair state, the entirety of $R^1$, $R^2$, and $R^3$ preferably has a branch structure content of 10 mol % or more, more preferably 20 mol % or more. From the viewpoint of the effect of restoring the hydrophobicity of the hair surface, the branch structure content is 70 mol % or less, preferably 60 mol % or less. From the viewpoint of the effect of restoring low friction in a wet hair state and the hydrophobicity of the hair surface, $R^1$, $R^2$, and $R^3$ preferably have both a linear chain and a branched chain structure.

The polyalkyleneimine derivative of component (a) may be synthesized through addition of substituents represented by formulas (I), (II), and (III) individually. In one procedure, a substituent (I) is added to the polyalkyleneimine, to thereby yield an acylated polyalkyleneimine, and a substituent (II) is added to the acylated polyalkyleneimine. If needed, a substituent (III) is further added. Notably, the order of addition of the substituents (I), (II), and (III) may be determined as desired.

The polyalkyleneimine derivative of component (a) may be a salt form. Practically, a salt of the polyalkyleneimine derivative may also formed in the hair cosmetic composition of the present invention, by adding an acid for modifying the pH to the composition. Examples of the acid include acids having an alkyl group such as a fatty acid, an alkylphosphoric acid, an alkylsulfonic acid, and an alkylsulfuric acid; acidic amino acids such as L-glutamic acid and L-aspartic acid; pyroglutamic acid; aromatic acids such as benzoic acid and p-toluenesulfonic acid; hydroxyacids such as glycolic acid, lactic acid, glyceric acid, gluconic acid, pantothenic acid, malic acid, tartaric acid, and citric acid; other acids including phosphoric acid, hydrochloric acid, acetic acid, and succinic acid. Of these, from the viewpoint of the effect of moisturizing and softening hair, organic acids are preferred. Particularly, acidic amino acids, pyroglutamic acid, and hydroxyacids are preferred, with hydroxyacids being more preferred.

The polyalkyleneimine derivative or a salt thereof (component (a)) is preferably water-insoluble at ambient temperature. The expression "component (a) is water-insoluble at ambient temperature" refers to the state in which component (a) added to pure water at 25° C. so as to have a concentration of at least 0.1% by mass is not dissolved to form a transparent solution, regardless of addition of an acid for neutralization (wherein the amount of the acid for neutralizing component (a) is not greater than the amount by equivalent of amino groups of component (a)). The expression "not dissolved to form a transparent solution" refers to the state in which a solution contains no solid such as aggregates or sediments which can be visually detected, and has a transmittance of 80% or more at 25° C. and 600 nm.

For restoring the hydrophobicity and low friction in a wet hair state, component (a) preferably tends to spontaneously take a conformation for realizing high alkyl group packing.

Conventionally, the alkyl group packing property has been studied. Specifically, there has been measured the π-A isotherm of a polypropyleneimine dendrimer (Aihua Su et al., J. Phys. Chem. C 2007, 111, pp. 4695-4701) formed through incorporation of an alkyl group into an alkyl group-introduced PAMAM dendrimer (Tracy Zhang et al., Langmuir 2007, 23, pp. 10589-10597). It is reported that an amido group bonded to the foot of an alkyl group provides a hydrogen bond which enhances the alkyl group packing property.

The present inventors estimate that when the polyalkyleneimine derivative or a salt thereof has a specific molecular weight and alkyl group density, the alkyl group packing property can be enhanced. The inventors also assume that an excellent alkyl group packing property is a key to expression of hydrophobicity and low friction in a wet state.

The degree of alkyl group packing property may be assessed by measuring the π-A isotherm of the polyalkyleneimine derivative or a salt thereof, to thereby calculate the occupation area of one alkyl group.

Component (a) exhibits high alkyl group packing property. More specifically, according to the measured π-A isotherm, the occupation area of one alkyl group is small under low-pressure conditions, such as a surface pressure of 0.1 mN/m. In other words, according to the measured π-A isotherm of component (a), the occupation area of one alkyl group at a surface pressure of 0.1 mN/m is preferably 17 (Å²) or less, more preferably 15 (Å²) or less, still more preferably 13 (Å²) or less.

Specific members of component (a) may be used singly or in combination of two or more species. In order to realize uniform adsorption of a thin layer of the cosmetic composition on the hair end surface having excessive hydrophilicity due to damage, so as to restore, in particular, water repellency of hair and low friction in a wet state, the component (a) content is preferably 0.05% by mass or higher with respect to the gel-form hair cosmetic composition of the present invention, more preferably 0.1% by mass or higher, still more preferably 0.2% by mass or more, and preferably 10.0% by mass or less, more preferably 3.0% by mass or less, still more preferably 1.0% by mass or lower, yet more preferably 0.8% by mass or less.

[Component (b): Saturated Aliphatic Alcohol]

Component (b) is a C12 to C28 saturated aliphatic alcohol. From the viewpoint of enhancing uniformity in adsorption of component (a) to hair and stability of the hair cosmetic composition, a C12 to C22 saturated aliphatic alcohol is preferred. Specific examples include lauryl alcohol, myristyl alcohol, cetyl alcohol, stearyl alcohol, and behenyl alcohol. Specific members of component (b) may be used singly or in combination of two or more species. The component (b) content is preferably 0.1% by mass or more with respect to the gel-form hair cosmetic composition of the present invention, more preferably 0.5% by mass or more, still more preferably 1.0% by mass or more, yet more preferably 2.0% by mass or more, yet more preferably 3.0% by mass or more, further more preferably 4.0% by mass or more, and preferably 20% by mass or less, more preferably 15% by mass or less, still more preferably 10% by mass or less.

[Component (c): Cationic Surfactant]

Examples of the cationic surfactant serving as component (c) include a tertiary amine derivative or a salt thereof, and a quaternary ammonium salt.

Examples of the tertiary amine derivative or a salt thereof include compounds selected from (i) an ether amine or a salt thereof and (ii) an amidoamine or a salt thereof.

The ether amine (i) is represented by the following formula (IV):

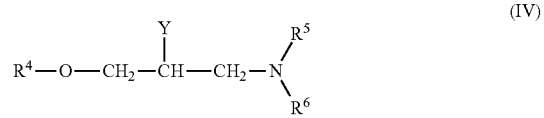

[wherein $R^4$ represents a C6 to C24 linear or branched alkyl group or alkenyl group; $R^5$ and $R^6$, which may be identical to or different from each other, each represent a C1 to C6 alkyl group or a -$(A^1O)_mH$ (wherein $A^1$ represents a C2 to C4 alkylene group; m is a number of 1 to 6; m of $A^1O$ moieties may be identical to or different from one another; and the sequence of the moieties is not limited); and Y is a hydrogen atom or a hydroxyl group].

Specific examples of preferred ether amines and salts thereof include N,N-dimethyl-3-hexadecyloxypropylamine or a salt thereof, N,N-dimethyl-3-octadecyloxypropylamine or a salt thereof, hexadecyloxy(2-hydroxypropyl)dimethylamine or a salt thereof, and octadecyloxy(2-hydroxypropyl)dimethylamine or a salt thereof. Among them, N,N-dimethyl-3-octadecyloxypropylamine or a salt thereof, and octadecyloxy(2-hydroxypropyl)dimethylamine or a salt thereof are more preferred.

The amidoamine (ii) is represented by the following formula (V):

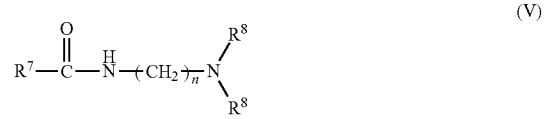

[wherein $R^7$ represents a C17 to C21 linear or branched alkyl group; two $R^8$s each represent the same C1 to C4 alkyl group; and n is a number of 2 to 4].

Specific examples of preferred amidoamines and salts thereof include stearic acid dimethylaminoethylamide or a salt thereof, stearic acid dimethylaminopropylamide or a salt thereof, stearic acid diethylaminoethylamide or a salt thereof, stearic acid diethylaminopropylamide or a salt thereof, stearic acid dipropylaminoethylamide or a salt thereof, stearic acid dipropylaminopropylamide or a salt thereof, behenic acid dimethylaminopropylamide or a salt thereof, and behenic acid diethylaminopropylamide or a salt thereof. Among them, stearic acid dimethylaminopropylamide or a salt thereof, stearic acid diethylaminoethylamide or a salt thereof, behenic acid dimethylaminopropylamide or a salt thereof, and behenic acid diethylaminopropylamide or a salt thereof are more preferred.

Specific examples of the quaternary ammonium salt include those represented by the following formulas (VI) and (VII).

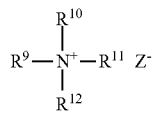

(VI)

[wherein at least one of $R^9$, $R^{10}$, $R^{11}$, and $R^{12}$ represents an alkoxy group, an alkenyloxy group, or an alkyl group or alkenyl group which may be substituted by an alkanoylamino group or an alkenoylamino group, these group having 8 to 28 carbon atoms in total, and each of the remaining groups represents a benzyl group or a C1 to C5 alkyl group or hydroxyalkyl group; and $Z^-$ represents an anion].

Among $R^9$, $R^{10}$, $R^{11}$, and $R^{12}$, $R^9$ is preferably a non-substituted alkyl group or an alkyl group substituted by an alkoxy group, each having 12 to 24 carbon atoms in total, more preferably 16 to 22 carbon atoms in total. Each of $R^{10}$, $R^{11}$, and $R^{12}$ is preferably an alkyl group having 1 to 5 carbon atoms in total. Examples of the anion $Z^-$ include halide ions such as chloride ion and bromide ion; and inorganic and organic anions such as methosulfate ion, ethosulfate ion, methophosphate ion, ethophosphate ion, and methocarbonate ion. Of these, halide ions are preferred, with chloride ion being more preferred.

Specific examples of preferred quaternary ammonium salts represented by formula (VI) include cetyltrimethylammonium salts, stearyltrimethylammonium salts, behenyltrimethylammonium salts, cetyloxypropyltrimethylammonium salts, and stearoxypropyltrimethylammonium salts.

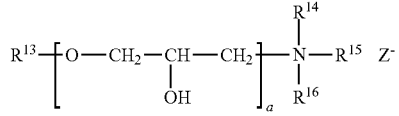

(VII)

[wherein $R^{13}$ represents a C6 to C24 linear or branched alkyl group or alkenyl group; $R^{14}$, $R^{15}$, and $R^{16}$, which may be identical to or different from one another, each represent a C1 to C6 alkyl group or a -$(A^2O)_b$H (wherein $A^2$ represents a C2 to C4 alkylene group; b is an integer of from 1 to 6; b of $A^2O$ moieties may be identical to or different from one another; and the sequence of the moieties is not limited); a is a number of from 1 to 5; and $Z^-$ represents an anion].

Specific examples of preferred quaternary ammonium salts represented by formula (VII) include hexadecyloxy(2-hydroxypropyl)trimethylammonium salts and octadecyloxy(2-hydroxypropyl)trimethylammonium salts.

Other than the cationic surfactants represented by formulas (IV) to (VII), examples of other cationic surfactants include lanolin fatty acid aminopropylethyldimethylammonium ethyl sulfate, lanolin fatty acid aminoethyltriethylammonium ethyl sulfate, lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic ($C_{14}$ to $C_{20}$) acid aminopropylethyldimethylammonium ethyl sulfate, isoalkanoic ($C_{18}$ to $C_{22}$) acid aminopropylethyldimethylammonium ethyl sulfate, isostearic acid aminopropylethyldimethylammonium ethyl sulfate, isononanoic acid aminopropylethyldimethylammonium ethyl sulfate, alkyltrimethylammonium saccharin, cetylpyridinium chloride, lauroylamidoethylguanidine hydrochloride, and N-palm oil fatty acid acyl-L-arginine ethyl DL-pyrrolidonecarboxylate.

Specific members of component (c) may be used singly or in combination of two or more species. Component (c) is preferably an ether amine or a salt thereof, or an amidoamine or a salt thereof. Of these, an ether amine or a salt thereof is preferred. The component (c) content, with respect to the hair cosmetic composition of the present invention, is preferably 0.01% by mass or more, more preferably 0.1% by mass or more, still more preferably 0.5% by mass or more, and preferably 20% by mass or less, more preferably 15% by mass or less, still more preferably 10% by mass or less, yet more preferably 5% by mass or less, further more preferably 2.5% by mass or less.

[Ratio of Component (b) to Component (c)]

In the gel-form hair cosmetic composition of the present invention, from the viewpoint of enhancing the stability of the gel-form hair cosmetic composition of the present invention, the ratio in amount of component (b) to component (c); i.e., the ratio by mole of component (b) to component (c) [(b)/(c)], is preferably 2.0 or more, more preferably 2.5 or more, and preferably 10.0 or less, more preferably 8.0 or less, still more preferably 6.0 or less.

[Oily Agent and Solvent Having a Solubility Parameter δ of 20 or Lower]

From the viewpoints of the stability of the composition and uniform adsorption of component (a) to hair, the gel-form hair cosmetic composition of the present invention is preferably free from an oily agent or a solvent which is liquid at ambient temperature and has non-volatility. The amount of such an oily agent or a solvent is preferably less than the amount which allows component (a) to be dissolved therein; i.e., less than the amount which would cause an adverse effect due to dissolution of component (a). The term "non-volatility" refers to a state in which the boiling point is 300° C. or higher at 25° C. and 1,013 hPa.

Such an oily agent or a solvent is one having a solubility parameter δ of 20 or less, except for a silicone, an oily agent or a solvent having a perfluoroalkyl group, and an amine. The solubility parameter δ (unit: $J^{1/2}$ cm$^{-3/2}$) refers to an estimated value calculated from the following equation.

$$\delta=(\Delta E_v/V_m)^{1/2}$$

$\Delta E_v$ [unit: kJmol$^{-1}$]: energy of vaporization per mole of liquid $V_m$ [unit: cm$^3$mol$^{-1}$]: molar volume $\Delta E_v=2.54\times10^{-4}T_b^2$ $T_b$ [unit: K]: boiling point as measured In the case where the boiling point of the target compound has not been measured, $T_b$ may be calculated from the boiling point T[K] at a pressure p[mmHg] of measurement according to the following equation.

$$T_b = \{T^\alpha + (760^\alpha - p^\alpha)/A\}^{1/\alpha}$$

A=14.1
α=0.105

The boiling point $T_b$ of a sublimable or pyrolizable compound, which cannot be principally measured, may be estimated through a group contribution method by Hoy (Allan F. M. Barton, CRC Handbook of Solubility Parameters and Other Cohesion Parameters 2nd ed., CRC Press (1991), p. 165-167).

Specific examples of the oily agent or solvent having a solubility parameter δ of 20 or less include hydrocarbons such as squalane (δ=16.2), liquid paraffin (δ=16.4), and isopropyl palmitate (δ=17.2); and glycerides such as castor oil (δ=18.2), jojoba oil (δ=17.6), olive oil (δ=17.5), and high-oleic sunflower oil.

So long as an adverse effect due to dissolution of component (a) is avoided, the aforementioned oily agent or solvent which is liquid at ambient temperature and non-volatile may be incorporated into the gel-form hair cosmetic composition of the present invention, for enhancing the stability of the composition. In the gel-form hair cosmetic composition of the present invention, the ratio by mass of the total amount of the aforementioned oily agent and/or solvent to the amount of component (a) is preferably 20 or less, more preferably 10 or less, still more preferably 5 or less, and preferably 0.01 or more, more preferably 0.1 or more. The total amount of the aforementioned oily agent and/or solvent with respect to the gel-form hair cosmetic composition of the present invention is preferably 4.0% by mass or less, more preferably 2.0% by mass or less, still more preferably 1.5% by mass or less, and preferably 0.01% by mass or more, more preferably 0.1% by mass or more.

[Gel]

The hair cosmetic composition of the present invention is a gel-form composition. The term "gel-form" refers to a state in which the viscosity is from 250 mPa·s to 100,000 mPa·s as measured by means of a type-B viscometer at 30° C. The viscosity is preferably from 500 mPa·s to 100,000 mPa·s, more preferably from 1,000 mPa·s to 50,000 mPa·s. The viscosity may be determined by means of a TVB10 viscometer (product of Toki Sangyo Co., Ltd.) with a T-bar stage TS-10 (product of Toki Sangyo Co., Ltd.) under the following conditions:

viscosity range of from 250 mPa·s or more to less than 500 mPa·s may be determined under the condition of 30° C., rotor M1, rotation rate of 12 rpm, 1 min;

viscosity range of from 500 mPa·s or more to less than 1,000 mPa·s may be determined under the condition of 30° C., rotor M2, rotation rate of 30 rpm, 1 min;

viscosity range of from 1,000 mPa·s or more to less than 2,500 mPa·s may be determined under the condition of 30° C., rotor M2, rotation rate of 12 rpm, 1 min;

viscosity range of from 2,500 mPa·s or more to less than 4,000 mPa·s is determined under the condition of 30° C., rotor M3, rotation rate of 30 rpm, 1 min;

viscosity range of from 4,000 mPa·s to less than 10,000 mPa·s is determined under the condition of 30° C., rotor M3, rotation rate of 12 rpm, 1 min;

viscosity range of from 10,000 mPa·s or more to less than 20,000 mPa·s is determined under the condition of 30° C., rotor M4, rotation rate of 30 rpm, 1 min; and viscosity range of 20,000 mPa·s or more is determined under the condition of 30° C., rotor T-C, rotation rate of 10 rpm, stage elevation rate: 20 mm/min, 1 min.

Next, the phase transition temperature of the gel formed by the hair cosmetic composition of the present invention will be described. From the viewpoint of mobility of the gel so as to facilitate release of component (a) from the gel, to thereby enhance adsorption of the gel on hair and attain hydrophobicity and low friction, the gel formed by the composition has an endothermic peak temperature, measured by means of a differential scanning calorimeter (DSC), of 75° C. or less, preferably 70° C. or less. From the viewpoint of the stability of the composition containing component (a), the endothermic peak temperature of the gel is 40° C. or more, preferably 50° C. or more.

[Silicones]

The hair cosmetic composition of the present invention may contain a silicone. Examples of the silicone include the following (i) to (vi).

(i) High-Polymerization Dimethylpolysiloxane

Examples of the high-polymerization dimethylpolysiloxane include a dimethylpolysiloxane having a polymerization degree of 1,000 or more. Specific examples include BY11-026, BY22-19, and FZ-3125 (products of Dow Corning Toray).

In use, the high-polymerization dimethylpolysiloxane may be dissolved or dispersed in a liquid oil (e.g., (ii) dimethylpolysiloxane, (iii) liquid silicone oil such as cyclic silicone, or liquid hydrocarbon oil such as isoparaffin).

(ii) Dimethylpolysiloxane Represented by the Following Formula:

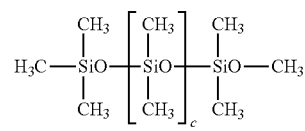

[F5]

[wherein c is an integer of from 0 to 1,000].

Specifically, the dimethylpolysiloxane represented by the above formula assumes liquid or oil. Examples of the dimethylpolysiloxane represented by the above formula include commercial products such as SH 200C series (viscosity 1 cs, 50 cs, 200 cs, 1000 cs, and 5000 cs, product of Dow Corning Toray).

(iii) Cyclic Silicone Represented by the Following Formula:

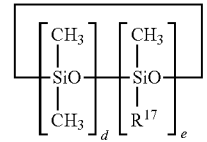

[wherein $R^{17}$ represents a C2 to C12 hydrocarbon group; a plurality of $R^{17}$s may be identical to or different from one another unit to unit; d is an integer of 1 or more; e is an integer of 0 or more; and d+e is 3 to 10].

Examples of the group represented by $R^{17}$ include linear or branched saturated hydrocarbon groups. $R^{17}$ is preferably a C2 to C10 hydrocarbon group, more preferably a C2 to C8 hydrocarbon group, still more preferably a C2 to C5 hydrocarbon group. The parameter d is preferably an integer of from 3 to 8, more preferably an integer of from 4 to 8, still more preferably an integer of from 4 to 6. The parameter e is preferably an integer of from 0 to 7, more preferably an integer of from 0 to 5, still more preferably an integer of from 0 to 3. The sum d+e is preferably from 3 to 8, more preferably from 4 to 8, still more preferably from 4 to 6.

Examples of the above cyclic silicone include SH 244, SH 344, SH 245, DC 345, and DC 246 (products of of Dow Corning Toray), and KF-994, KF-995, and KF-9937 (products of Shin-Etsu Chemical Co., Ltd.).

(iv) Amino-Modified Silicone

Examples of the amino-modified silicone include silicones represented by the following formula:

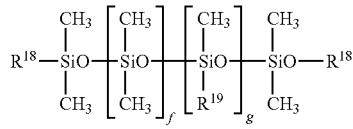

[wherein $R^{18}$ represents a methyl group, a hydroxyl group, or $R^{20}$-T (wherein $R^{20}$ represents a C3 to C6 alkylene group, and T represents a group having a primary to tertiary amino group or a group having an ammonium group); $R^{19}$ represents —$R^{21}$-Q (wherein $R^{21}$ represents a C3 to C6 alkylene group, and Q represents a group having a primary to tertiary amino group or a group having an ammonium group); f is an integer of 1 or more; and g is an integer of 0 or more. When g is 0, $R^{18}$ is —$R^{20}$-T. The average molecular weight is preferably from 3,000 to 100,000].

Examples of the amino-modified silicone represented by the above formula include SS-3551, SF8452C, DC929, and DC 8500 (products of Dow Corning Toray); and KT1989 (product of Momentive Performance Materials Inc.). When the amino-modified silicone is used as an aqueous emulsion, the aqueous emulsion preferably has an amino-modified silicone content of from 20 to 60% by mass, more preferably from 30 to 50% by mass. Examples of preferred aqueous amino-modified silicone emulsions include SM8704C (product of Dow Corning Toray).

Other examples of the amino-modified silicone include an amino-modified polysiloxane-polyoxyalkylene block copolymer represented by the following formula, which is a "8500 Conditioning Agent" (CAS No. 237753-63-8, product Dow Corning Toray).

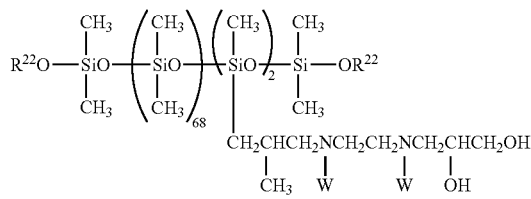

[wherein $R^{22}$ is a C13 to C15 linear or branched alkyl group; 75% of groups W represent —$CH_2CH(OH)CH_2OH$, and 25% thereof a hydrogen atom].

Examples of preferred amino-modified polysiloxane-polyoxyalkylene block copolymer include such copolymers represented by the following formula:

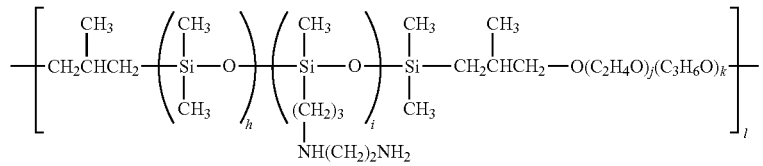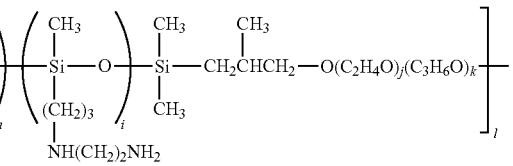

[wherein h is an integer of 2 or more; i is an integer of 1 or more; j is an integer of 4 or more; k is an integer of from 0 to 30; and l is an integer of 2 or more].

In the above formula, preferably, h is a number of from 2 to 1,000; i is a number of from 1 to 50; j is a number of from 4 to 200; and l is a number of from 2 to 100. The polymer —$O(C_2H_4O)_j(C_3H_6O)_k$— may be a block copolymer or a random copolymer. Examples of commercial products thereof include FZ-3789 and silicone SS-3588 (products of Dow Corning Toray).

(v) Dimethiconol Represented by the Following Formula:

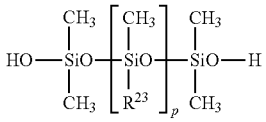

[wherein $R^{23}$ represents a methyl group or a phenyl group; and p is an integer of from 1 to 20,000]

Examples of commercial products of such a dimethiconol include XF49-C2070 and XF49-C2497 (products of Momentive Performance Materials Inc.); X21-5666, X21-5661, X-21-5613, and X-21-5849 (products of Shin-Etsu Chemical Co., Ltd.); and 1501 FLUID and 1503 FLUID (products of Dow Corning Toray).

(vi) Other Silicones

Other than the aforementioned examples, examples of the silicone ingredient include polyether-modified silicone, polyglycidol-modified silicone, methylphenylpolysiloxane, fatty acid-modified silicone, alcohol-modified silicone, alkloxy-modified silicone, epoxy-modified silicone, fluorine-modified silicone, and alkyl-modified silicone.

From the viewpoint of reducing friction of hair surface to improve hand combing smoothness and combing smoothness, the silicone content of the hair cosmetic composition of the present invention is preferably 0.1% by mass or more, more preferably 0.5% by mass or more, and preferably 15% by mass or less, more preferably 10% by mass or less.

Other Optional Ingredients

Into the hair cosmetic composition of the present invention, other ingredients generally employed in hair cosmetic compositions may be incorporated in accordance with purposes. Examples of optional ingredients include polymers such as cationized cellulose, hydroxylated cellulose, and high-polymerization polyethylene oxide; nonionic surfactants such as polyoxyethylene alkyl ether, polyoxyethylene sorbitan fatty acid ester, glycerin fatty acid ester, polyglycerin fatty acid ester, polyoxyethylene hardened castor oil, sucrose fatty acid ester, polyglycerin alkyl ether, fatty acid alkanolamide, and alkylglycoside; hydrocarbons such as squalene, squalane, liquid paraffin, liquid isoparaffin, and cycloparaffin; glycerides such as castor oil, cacao oil, mink oil, avocado oil, and olive oil; waxes such as beeswax, spermaceti, lanolin, and carnauba wax; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanate, and tridecyl isononanate; higher fatty acids such as capric acid, lauric acid, myristic acid, palmitic acid, stearic acid, behenic acid, oleic acid, coconut fatty acid, isostearic acid, and isopalmitic acid; oily agents such as isostearyl glyceryl ether and polyoxypropylene butyl ether; alcohols such as ethanol, 1-propanol, 2-propanol, butanol, ethylene glycol, propylene glycol, benzyl alcohol, phenoxyethanol, 2-benzyloxyethanol, methyl carbitol, ethyl carbitol, propyl carbitol, butyl carbitol, triethylene glycol monoethyl ether, triethylene glycol monobutyl ether, and glycerin; anti-dandruff agents such as zinc pyrithione and benzalkonium chloride; vitamins; antibacterials; anti-inflammatory agents; antiseptics; chelating agents; humectants such as panthenol; colorants such as a dye and a pigment; extracts such as *Eucalyptus Globulus* polar solvent extract, a protein or a hydrolyzate thereof obtained from shells having a nacreous layer or pearl, a protein or a hydrolyzate thereof obtained from silk, a protein-containing extract obtained from seeds of leguminous plant, *Panax ginseng* extract, rice germ extract, Fucus extract, *Camellia* extract, Aloe extract, *Alpinia zerumbet* leaf extract, and *Chlorella Vulgaris* extract; pearl powder products such as titanated mica; refrigerants such as menthol; perfumes; dyes; UV-absorbers; antioxidants; and other ingredients disclosed in ENCYCLOPEDIA OF SHAMPOO INGREDIENTS (MICELLE PRESS).

These ingredients include the aforementioned oily agent or solvent which is liquid at ambient temperature and has non-volatility; i.e., an oily agent and a solvent having a solubility parameter δ of 20 or less. However, as described above, such ingredients may be used, so long as an adverse effect due to dissolution of component (a) is avoided.

[pH]

From the viewpoint of enhancing the stability of the hair cosmetic composition of the present invention, the pH of the hair cosmetic composition is preferably 2.0 or more, more preferably 2.5 or more, still more preferably 3.0 or more. From the viewpoint of enhancing adsorption of component (a) onto hair, the pH is preferably 7.5 or less, more preferably 6.5 or less, still more preferably 5.5 or less. Notably, in the present invention, the pH of the hair cosmetic composition is defined as a pH value of a 20-fold (by mass) water dilution of the composition determined at 25° C.

[Forms of the Hair Cosmetic Composition]

Examples of the form of the gel-form hair cosmetic composition of the present invention include bath products such as a hair conditioner, a hair treatment, and a hair pack; and out-bath styling materials such as hair milk, hair cream, and hair wax.

[Hair Modifying Method]

Through treatment of hair with the gel-form hair cosmetic composition of the present invention, a conditioning base of the composition can be uniformly adsorbed on the hair end surface that has been damaged to have hydrophilicity, whereby the hydrophobicity intrinsic to healthy hair and low hair friction in a wet state can be restored. For improving hydrophobicity and low friction of hair, the gel-form hair cosmetic composition of the present invention is applied to the hair, and sufficiently spread over the hair. In the case where the gel-form hair cosmetic composition is a wash-out type agent, the gel-form hair cosmetic composition is applied to and spread over the hair, and the composition is then rinsed off.

In addition to the aforementioned embodiments of the invention, further preferred embodiments will next be described.

<1>

A gel-form hair cosmetic composition, which is a gel-form aqueous composition containing the following components (a), (b), and (c) emulsified in an aqueous component, which gel exhibits an endothermic peak temperature of from 40° C. or more to 75° C. or less as measured by means of a differential scanning calorimeter (DSC).

(a) A polyalkyleneimine derivative or a salt thereof, the polyalkyleneimine derivative being formed of a polyalkyleneimine having a weight average molecular weight of from 3,300 or more to 50,000 or less, in which at least one of the substituents represented by any of formulas (I), (II), and (III) is bonded to 40 mol % or more of the nitrogen atoms of the polyalkyleneimine, the formulas being:

$$R^1-CO- \quad (I)$$

$$R^2-(CH_2)_n-CHX-CH_2- \quad (II)$$

$$R^3-NH-CO- \quad (III)$$

[wherein, in formula (I), $R^1$ represents a group selected from the group consisting of a hydrogen atom, and an alkyl group, an alkenyl group, and a hydroxyalkyl group, in the form of a linear chain group or a branched chain group;

in formula (II), $R^2$ represents a group selected from the group consisting of a hydrogen atom, and an alkyl group, an alkoxy group, an alkenyl group, and an alkenyloxy group, in the form of a linear chain group or a branched chain group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;

in formula (III), $R^3$ represents a group selected from the group consisting of a hydrogen atom, and an alkyl group and an alkenyl group, in the form of a linear chain group or a branched chain group; and $R^1$, $R^2$, and $R^3$ may be identical to or different from one another, and at least one of $R^1$, $R^2$, and $R^3$ is a group having 13 or more carbon atoms; the entirety of $R^1$, $R^2$, and $R^3$ has an average number of carbon atoms of 9 or greater; and the entirety of $R^1$, $R^2$, and $R^3$ has a linear group content of 30 mol % or greater];

(b) a C12 to C28 saturated aliphatic alcohol; and (c) a cationic surfactant.

<2>

The gel-form hair cosmetic composition as described in <1>, wherein, in component (a), the ratio of the number of nitrogen atoms, which atoms are bonded to a substituent represented by any of formulas (I), (II), and (III), to the number of all nitrogen atoms of the polyalkyleneimine is preferably 45 mol % or more, more preferably 50 mol % or more.

<3>

The gel-form hair cosmetic composition as described in <1> or <2>, wherein, in component (a), the ratio of the number of groups represented by formula (I) to the number of all substituents is preferably 20 mol % or more, more preferably 40 mol % or more, still more preferably 60 mol % or more, yet more preferably 80 mol % or more, and the ratio of the total number of groups represented by formulas (II) and (III) to the number of all substituents is preferably 80 mol % or less, more preferably 60 mol % or less, still more preferably 40 mol % or less, yet more preferably 20 mol % or less.

<4>
The gel-form hair cosmetic composition as described in any of <1> to <3>, wherein, in component (a), the entirety of $R^1$, $R^2$, and $R^3$ preferably has a linear structure content of 40 mol % or more, and 90 mol % or less, preferably 80 mol % or less.

<5>
The gel-form hair cosmetic composition as described in any of <1> to <4>, wherein, in component (a), the entirety of $R^1$, $R^2$, and $R^3$ preferably has a branch structure content of 10 mol % or more, more preferably 20 mol % or more, and 60 mol % or less.

<6>
The gel-form hair cosmetic composition as described in <4>, wherein, in component (a), the entirety of $R^1$, $R^2$, and $R^3$ preferably has a linear structure content of 30 mol % or more to 90 mol % or less and a branch structure content of 10 mol % or more to 70 mol % or less.

<7>
The gel-form hair cosmetic composition as described in <4>, wherein, in component (a), the entirety of $R^1$, $R^2$, and $R^3$ preferably has a linear structure content of 40 mol % or more to 80 mol % or less and a branch structure content of 20 mol % or more to 60 mol % or less.

<8>
The gel-form hair cosmetic composition as described in any of <1> to <7>, wherein, in component (a), the entirety of $R^1$, $R^2$, and $R^3$ preferably has an average number of carbon atoms of 12 or more.

<9>
The gel-form hair cosmetic composition as described in any of <1> to <8>, wherein the polyalkyleneimine, which is a source of component (a), preferably has a weight average molecular weight of 4,000 or more, more preferably 4,500 or more, still more preferably 5,000 or more, and preferably 40,000 or less, more preferably 30,000 or less, still more preferably 20,000 or less, yet more preferably 10,000 or less.

<10>
The gel-form hair cosmetic composition as described in any of <1> to <9>, wherein the polyalkyleneimine, which is a source of component (a), preferably has a tertiary amino group content of the polyethyleneimine, based on the total amount of nitrogen atoms, of 10 mol % or more, more preferably 20 mol % or more, still more preferably 25 mol % or more, and preferably 40 mol % or less, more preferably 35 mol % or less.

<11>
The gel-form hair cosmetic composition as described in any of <1> to <10>, wherein the polyalkyleneimine derivative or a salt thereof, which is component (a), preferably has a weight average molecular weight of 2,500 or more, more preferably 3,000 or more, still more preferably 3,500 or more, and preferably 50,000 or less, more preferably 40,000 or less, still more preferably 20,000 or less, yet more preferably 10,000 or less.

<12>
The gel-form hair cosmetic composition as described in any of <1> to <11>, wherein the component (a) content is preferably 0.05% by mass or more, more preferably 0.1% by mass or more, still more preferably 0.2% by mass or more, and preferably 10.0% by mass or less, more preferably 3.0% by mass or less, still more preferably 1.0% by mass or less, yet more preferably 0.8% by mass or less.

<13>
The gel-form hair cosmetic composition as described in any of <1> to <12>, wherein component (b) is preferably a C12 to C22 saturated aliphatic alcohol.

<14>
The gel-form hair cosmetic composition as described in <13>, wherein component (b) is selected from the group consisting of lauryl alcohol, myristyl alcohol, cetyl alcohol, stearyl alcohol, and behenyl alcohol.

<15>
The gel-form hair cosmetic composition as described in any of <1> to <14>, wherein the component (b) content is preferably 0.1% by mass or more, more preferably 0.5% by mass or more, still more preferably 1.0% by mass or more, yet more preferably 2.0% by mass or more, yet more preferably 3.0% by mass or more, further more preferably 4.0% by mass or more, and preferably 20% by mass or less, more preferably 15% by mass or less, still more preferably 10% by mass or less.

<16>
The gel-form hair cosmetic composition as described in any of <1> to <15>, wherein component (c) is preferably selected from the group consisting of an ether amine or a salt thereof, an amidoamine or a salt thereof, and a quaternary ammonium salt.

<17>
The gel-form hair cosmetic composition as described in any of <1> to <16>, wherein the component (c) content is preferably 0.01% by mass or more, more preferably 0.1% by mass or more, still more preferably 0.5% by mass or more, and preferably 20% by mass or less, more preferably 15% by mass or less, still more preferably 10% by mass or less, yet more preferably 5% by mass or less, further more preferably 2.5% by mass or less.

<18>
The gel-form hair cosmetic composition as described in any of <1> to <17>, wherein the ratio by mole of component (b) to component (c) [(b)/(c)] is preferably 2.0 or more, more preferably 2.5 or more, and preferably 10.0 or less, more preferably 8.0 or less, still more preferably 6.0 or less.

<19>
The gel-form hair cosmetic composition as described in any of <1> to <18>, wherein the ratio of the total amount of the non-volatile solvent and oily agent which are liquid at ambient temperature and have a solubility parameter δ of 20 or less to the amount of component (a) is preferably 20 or less, more preferably 10 or less, still more preferably 5 or less, and preferably 0.01 or more, more preferably 0.1 or more.

<20>
The gel-form hair cosmetic composition as described in any of <1> to <19>, wherein the total amount of the non-volatile solvent and oily agent which are liquid at ambient temperature and have a solubility parameter δ of 20 or less is preferably 4.0% by mass or less, more preferably 2.0% by mass or less, still more preferably 1.5% by mass or less, and preferably 0.01% by mass or more, more preferably 0.1% by mass or more.

<21>
The gel-form hair cosmetic composition as described in any of <1> to <20>, which preferably has a pH of 2.0 or more, more preferably 2.5 or more, still more preferably 3.0 or more, and preferably 7.5 or less, more preferably 6.5 or less, still more preferably 5.5 or less, at 25° C. when diluted 20-fold by mass with water.

<22>
A method for modifying hair, comprising applying to hair a gel-form hair cosmetic composition as recited in any of <1> to <21>, and spreading the composition over the hair.
<23>
A method for modifying hair, comprising applying to hair a gel-form hair cosmetic composition as recited in any of <1> to <21>, spreading the composition over the hair, and rinsing off the composition.
<24>
Use of a gel-form hair cosmetic composition as recited in any of <1> to <21> for restoring the hydrophobicity of hair that has been damaged to have hydrophilicity by applying the composition to and spreading over the hair.
<25>
Use of a gel-form hair cosmetic composition as recited in any of <1> to <21> for restoring low friction of hair by applying the composition to and spreading over the hair.
<26>
Use of a gel-form hair cosmetic composition as recited in any of <1> to <21> for restoring the hydrophobicity of hair that has been damaged to have hydrophilicity by applying the composition to and spreading over the hair, and then rinsing off the composition.
<27>
Use of a gel-form hair cosmetic composition as recited in any of <1> to <21> for restoring low friction of hair by applying the composition to and spreading over the hair, and then rinsing off the composition.

EXAMPLES

Production Example 1: Polyalkyleneimine Derivative (1)

Polyethyleneimine (EPOMIN SP018, molecular weight: 1,800 (manufacturer's nominal value), product of Nippon Shokubai, Co., Ltd.) (40 g) was heated, and stearic acid (Lunac S-98; product of Kao Corporation) (140 g) was added thereto. Under a stream of nitrogen, the mixture was heated to 180° C. and stirred for 18 hours, to thereby yield polyethyleneimine derivative (1) in which 50 mol % of the nitrogen atoms of polyethyleneimine were acylated.

Production Example 2: Polyalkyleneimine Derivative (2)

The procedure of Production Example 1 was repeated, except that polyethyleneimine (Lupasol PR$^{8515}$, molecular weight: 2,000 (manufacturer's nominal value), product of BASF) (40 g), stearic acid (Lunac S-98, product of Kao Corporation) (86.8 g), isostearic acid (52.1 g) (Isostearic acid EX, product of Kokyu Alcohol Kogyo Co., Ltd.), and acetic acid (11.7 g), to thereby yield polyethyleneimine derivative (2) in which 70% of the nitrogen atoms of polyethyleneimine were acylated. The derivative (2) was found to have a ratio by mole of linear-chain alkyl to branched-chain alkyl of 73:27.

Production Examples 3 to 11: Polyalkyleneimine Derivatives (3) to (11)

The procedures of Production Examples 1 and 2 were repeated, whereby reaction between polyalkyleneimine and fatty acid was performed, to thereby yield polyalkyleneimine derivatives (3) to (11).

Production Example 12: Polyalkyleneimine Derivative (12)

Polyethyleneimine (EPOMIN SP012, molecular weight: 1,200 (manufacturer's nominal value), weight average molecular weight (as measured): 4,250, product of Nippon Shokubai, Co., Ltd.) (40 g) was heated, and isostearyl glycidyl ether (disclosed in JP56-142275 A) (27 g) was added thereto. Under a stream of nitrogen, the mixture was heated to 80° C. and allowed to react for 4 hours. Subsequently, stearic acid (Lunac S-98, product of Kao Corporation) (100 g) was added to the reaction mixture. The resultant mixture was heated to 180° C. and allowed to react for 8 hours, to thereby yield polyethyleneimine derivative (12). In the derivative (12), about 9 mol % of the nitrogen atoms of polyethyleneimine were alkylated (i.e., bonded to a substituent represented by formula (II)) and about 36 mol % of the nitrogen atoms were acylated (i.e., bonded to a substituent represented by formula (I)).

Production Example 13: Polyalkyleneimine Derivative (13)

Polyethyleneimine (Lupasol G20 waterfree, molecular weight: 1,300 (manufacturer's nominal value), weight average molecular weight (as measured): 3,500, product of BASF (40 g) was dissolved in toluene (100 g), and the solution was heated to 100° C. under a stream of nitrogen. Octadecyl isocyanate (product of Wako Pure Chemical Industries, Ltd.) (49.4 g) was added dropwise to the heated solution, and the mixture was allowed to react for 4 hours. Subsequently, stearic acid (Lunac S-98, product of Kao Corporation) (42.2 g) and isostearic acid (Isostearic acid EX, product of Kokyu Alcohol Kogyo Co., Ltd.) (26.4 g) were added to the reaction mixture. While toluene was removed through distillation, the resultant mixture was heated to 180° C. and allowed to react for 8 hours, to thereby yield polyethyleneimine derivative (13). In the derivative (13), about 20 mol % of the nitrogen atoms of polyethyleneimine were ureated (i.e., bonded to a substituent represented by formula (III)) and about 30 mol % of the nitrogen atoms were acylated (i.e., bonded to a substituent represented by formula (I)).

Production Example 14: Polyalkyleneimine Derivative (14)

Polyethyleneimine (EPOMIN SP012, molecular weight: 1,200 (manufacturer's nominal value), weight average molecular weight (as measured): 4,250, product of Nippon Shokubai, Co., Ltd.) (40 g) was heated, and stearyl glycidy ether (72 g) and isostearyl glycidyl ether (disclosed in JP56-142275 A) (48 g) were added thereto. Under a stream of nitrogen, the mixture was heated to 80° C. and allowed to react for 8 hours, to thereby yield polyethyleneimine derivative (14). In the derivative (14), about 40 mol % of the nitrogen atoms of polyethyleneimine were alkylated (i.e., bonded to a substituent represented by formula (II)).

Table 1 shows data of polyalkyleneimine derivatives produced in Production Examples 1 to 14. The date include the molecular weights (manufacturer's nominal values, and measured weight average molecular weights) of polyethyleneimines serving as raw materials, the weight average molecular weights (as measured) of formed polyalkyleneimine derivatives, the nitrogen atom substitution ratios (mol %), the numbers of carbon atoms in $R^1$, $R^2$, and $R^3$, the average numbers of alkyl carbon atoms in the substituents, the C≥13 contents of the alkyl groups, and the linear/branch balances of the alkyl groups, and the specific substituent ratios.

The weight average molecular weights of the polyalkyleneimines and polyalkyleneimine derivatives were determined under the following conditions.

<Weight Average Molecular Weight Measurement Conditions>

Conditions 1 (Measurement Conditions for Polyalkyleneimines Serving as Raw Materials of Component (a))

Each polyalkyleneimine was dissolved in eluent 1, to thereby form a 0.1% by mass solution, and the solution was analyzed through GPC under the following conditions, whereby weight average molecular weights as reduced to pullulan were determined.

GPC Measurement Conditions

Column: two columns of TSK gel α-M (product of Tosoh Corporation)

Eluent 1: 0.15-mol/L sodium sulfate, 1% bymass acetic acid/water

Flow rate: 1.0 mL/min, column temperature: 40° C.

Detector: refractive index detector

Conditions 2 (Measurement Conditions for Component (a))

Each polyalkyleneimine derivative or a salt thereof was dissolved in eluent 2, to thereby form a 0.5% by mass solution, and the solution was analyzed through GPC under the following conditions, whereby weight average molecular weights as reduced to polystyrene were determined.

GPC Measurement Conditions

Column: two columns of K-804L (product of Shodex)

Eluent 2: 0.1-mol/L N,N-dimethyldodecylamine (Farmin DM2098 (product of Kao Corporation))/chloroform Flow rate: 1.0 mL/min, column temperature: 40° C.

Detector: refractive index detector

Examples 1 to 13, Comparative Examples 1 to 12

Gel-form hair cosmetic compositions having formulations shown in Tables 3 to 6 were prepared through a conventional method.

A gel was formed from each of the gel-form hair cosmetic compositions, and the endothermic peak temperature (° C.) of the gel was measured. Separately, each gel-form hair cosmetic composition was applied to damaged hair at a bath ratio of 20% by mass and spread over the hair for 30 seconds. The thus-treated hair was rinsed for 30 second in a flow of water. Thereafter, the friction coefficient in a wet state and the receding contact angle of the hair were measured. The methods of measurement are as follows.

Also, some tested polyalkyleneimine derivatives were evaluated in terms of the degree of alkyl group packing. The evaluation method will also be described below.

<Preparation of Tress Samples for Evaluation>

Black straight hair of a Japanese adult woman who had received no chemical treatment was cut into hair filaments having a length of about 25 cm. The hair filaments were immersed in an aqueous solution (20-fold diluted with water) of the below-described standard shampoo at from 40 to 50° C. for 10 minutes. The shampooed hair filaments were rinsed with a flow of water and then dried by air blow. The hair filaments (about 10 g) were layered on a substrate to a width of 4 cm so as to have a uniform layer thickness. One end of the hair layer was fixed to a plastic plate (width: 3 cm) with an adhesive so as to adjust the hair filament length to 20 cm. The thus-fabricated hair sample was subjected four times to bleaching, followed by 90 sets of washing after each bleaching procedure. After every five washing procedures, the hair of the hair sample was dried and subjected to setting for about 3 seconds by means of a hair iron at 180° C., from the root to the hair end. Thus, damaged hair tress samples

TABLE 1

| | | | (1) | (2) | (3) | (4) | (5) | (6) | (7) | (8) | (9) | (10) | (11) | (12) | (13) | (14) |
|---|---|---|---|---|---|---|---|---|---|---|---|---|---|---|---|---|
| Mol. wt. of raw material polyalkyleneimine | Nominal by manufacturer | | 1800 | 2000 | 1800 | 1200 | 1200 | 1800 | 10000 | 600 | 1800 | 1200 | 1800 | 1200 | 1300 | 1200 |
| | Wt. av. mol. wt. (GPC, as pullulan) | | 5650 | 4850 | 5650 | 4250 | 4250 | 5650 | 15800 | 3000 | 5650 | 4250 | 5650 | 4250 | 3500 | 4250 |
| Wt. av. mol. wt. of polyalkyleneimine derivative (GPC, as polystyrene) | | | 4450 | 3850 | 4350 | 3250 | 3200 | 4400 | 14900 | 2300 | 3950 | 2150 | 4400 | 3200 | 2500 | 3200 |
| Substitution ratio (mol %) | | | 50 | 70 | 60 | 40 | 60 | 50 | 60 | 40 | 20 | 50 | 50 | 45 | 50 | 40 |
| $R^1$ | C | $R^1$ | 17 | 1, 17 | 17 | 17 | 17 | 17, 19, 21 | 17 | 17 | 17 | 11 | 17 | 17 | 17 | — |
| $R^2$ | | $R^2$ | — | — | — | — | — | — | — | — | — | — | — | 18 | — | 18 |
| $R^3$ | | $R^3$ | — | — | — | — | — | — | — | — | — | — | — | — | 18 | — |
| | Av. C no. | | 17 | 12.4 | 17 | 17 | 17 | 18.9 | 17 | 17 | 17 | 11 | 17 | 17.2 | 17.4 | 18 |
| | C≥13 content (mol %) | | 100 | 71 | 100 | 100 | 100 | 100 | 100 | 100 | 100 | 0 | 100 | 100 | 100 | 100 |
| | Linear:branch | | 100:0 | 73:27 | 60:40 | 80:20 | 70:30 | 50:50 | 60:40 | 60:40 | 80:20 | 100:0 | 20:80 | 80:20 | 80:20 | 60:40 |
| | (I)/[(I) + (II) + (III)] | | 100 | 100 | 100 | 100 | 100 | 100 | 100 | 100 | 100 | 100 | 100 | 80 | 60 | 0 |
| | (II)/[(I) + (II) + (III)] | | 0 | 0 | 0 | 0 | 0 | 0 | 0 | 0 | 0 | 0 | 0 | 20 | 0 | 100 |
| | (III)/[(I) + (II) + (III)] | | 0 | 0 | 0 | 0 | 0 | 0 | 0 | 0 | 0 | 0 | 0 | 0 | 40 | 0 |

Mol. Wt. = Molecular weight;
Wt. av. mol. wt. = Weight average of molecular weight
Av. C. no. = Average carbon number;
C = Carbon number which had been subjected to bleaching (4 times), washing (360 times), and setting with a hair iron (72 times) were provided.

Standard Shampoo Formulation (pH 7.0)

|  | (% by mass) |
|---|---|
| 25% POE(2.5) lauryl ether sulfate sodium salt | 62.0 |
| Lauric acid diethanolamide | 2.3 |
| Disodium edetate | 0.15 |
| Sodium benzoate | 0.5 |
| Sodium chloride | 0.8 |
| 75% Phosphoric acid | q.s. |
| Perfume, methylparaben | q.s. |
| Purified water | balance |

<Measurement of Endothermic Peak Temperature by Means of Differential Scanning Calorimeter (DSC)>

Each gel-form aqueous composition (30 mg) and distilled water (a standard substance) (30 mg) were put into closable aluminum cells, respectively, and the cells were closed. The two cells were set in a holder of a differential scanning calorimeter (DSC 6100, product of SII Nanotechnology). The cells were heated from 30 to 90° C. at a temperature elevation rate of 2° C./rain, and the temperature at which heat absorption reached the maximum level during phase transition of the composition was recorded as a DSC endothermic peak temperature.

<Measurement of Dynamic Friction Coefficient in Wet State>

The friction of damaged hair after treatment with the gel-form hair cosmetic composition was evaluated in a hair wet state. The evaluation was performed according to the method disclosed in J. Soc. Cosmet. Chem. Japan, Vol. 15, No. 3, P. 225-232 (1985), Fuminori HARUSAWA et al. "Sorption of Active Agent on Hair and Fiber, and Coefficient of Dynamic Friction of Hair."

<Measurement of Receding Contact Angle after Hair Treatment>

Receding contact angle is known to drastically rise when a hydrophobic surface portion occupies an area ratio of about 80% or higher (Walter J. et al. "The Receding Contact Angle," Journal of Colloid and Interface Science, Vol. 33, No. 1, p. 164 (1970)). Thus, receding contact angle can be employed as an index for assessing uniformity in adsorption of a hydrophobic conditioning agent. Generally, a damaged hair end exhibits a receding contact angle of 0°, and a healthy hair filament exhibits a receding contact angle of 30 to 60°.

After treatment of hair tresses with the gel-form hair cosmetic composition, the receding contact angle (°) of hair tresses filaments (N=10) was measured according to the method disclosed in Shunsuke WATABE at al., "Adsorption behavior of silicone on hair," Journal of SCCJ, Vol. 29, No. 1, p. 64-68 (1995). Notably, the receding contact angle of the hair tresses before the treatment was 0°.

<Evaluation of Degree of Alkyl Group Packing Property in Polyalkyleneimine Derivative>

The alkyl group packing property in each of the polyalkyleneimine derivatives was assessed according to the method disclosed in Tracy Zhang et al. (3 other co-authors), Langmuir 2007, 23, pp. 10589-10597, by measuring a π-A isotherm of each of the polyalkyleneimine derivatives (3), (4), (7), (8), (9), and (14). Based on the isotherm, the occupation area of one alkyl group was calculated at a surface pressure of 0.1 mN/m. Table 2 shows the results.

TABLE 2

| Polyalkyleneimine derivative | Occupation area ($Å^2$) of one alkyl group at surface pressure of 0.1 mN/m |
|---|---|
| (3) | 10.6 |
| (4) | 9.0 |
| (7) | 12.2 |
| (8) | 17.4 |
| (9) | 21.8 |
| (14) | 11.5 |

TABLE 3

|  |  |  | Examples | | | | | | |
|---|---|---|---|---|---|---|---|---|---|
| (% by mass) |  |  | 1 | 2 | 3 | 4 | 5 | 6 | 7 |
| (a) | Polyalkyleneimine derivative | (1) | 0.2 |  |  |  |  |  |  |
|  |  | (2) |  | 0.5 |  |  |  |  |  |
|  |  | (3) |  |  | 0.2 |  |  |  |  |
|  |  | (4) |  |  |  | 0.2 |  |  |  |
|  |  | (5) |  |  |  |  | 0.2 |  |  |
|  |  | (6) |  |  |  |  |  | 0.8 |  |
|  |  | (7) |  |  |  |  |  |  | 0.2 |
| (b) | Cetyl alcohol |  | 1.5 |  | 2 | 2 | 2 | 5 | 4.5 |
|  | Stearyl alcohol |  | 2 | 8 | 2 | 2.5 | 2 | 4 |  |
|  | Behenyl alcohol |  |  |  |  |  |  | 1 |  |
| (c) | N,N-Dimethyl-3-octadecyloxypropylamine |  | 1 | 2 |  |  |  | 2.5 | 1 |
|  | Octadecyloxy(2-hydroxypropyl)dimethylamine |  |  |  |  |  |  |  | 0.2 |
|  | Behenylamidopropyldimethylamine |  |  |  | 1 |  |  |  |  |
|  | Stearamidopropyldimethylamine |  |  |  |  | 1 |  |  |  |
|  | Behenyltrimethylammonium chloride |  |  |  |  |  | 1 |  |  |
| Other | Benzyl alcohol |  | 0.5 | 0.4 | 0.2 | 0.5 |  |  | 0.5 |
|  | Dipropylene glycol |  |  | 3 |  |  | 2 |  | 2 |
|  | Isopropyl palmitate |  |  |  |  |  |  | 0.6 |  |
|  | High-oleic sunflower oil |  |  |  |  |  |  | 0.3 |  |
|  | 90% Lactic acid |  | 0.7 | 1.5 | 0.8 | 0.7 | 0.8 | 2 | 0.8 |
|  | Perfume |  | 0.5 | 0.5 | 0.5 | 0.5 | 0.5 | 0.5 | 0.5 |
|  | Sodium hydroxide |  | q.s. | q.s. | q.s. | q.s. | q.s. | q.s. | q.s. |
|  | Water |  | bal. | bal. | bal. | bal. | bal. | bal. | bal. |

TABLE 3-continued

| (% by mass) | Examples | | | | | | |
|---|---|---|---|---|---|---|---|
| | 1 | 2 | 3 | 4 | 5 | 6 | 7 |
| pH (20-fold (mass) water dilute, 25° C.) | 4.5 | 4.5 | 4.3 | 4.5 | 4.3 | 3.5 | 4.3 |
| DSC endothermic peak temp. (° C.) | 63 | 68 | 65 | 67 | 65 | 65 | 57 |
| Viscosity (mPa · s) | 24000 | 42000 | 24000 | 18000 | 21000 | 47000 | 24000 |
| Evaluation Friction coeff. in wet state | 0.37 | 0.18 | 0.21 | 0.25 | 0.24 | 0.19 | 0.23 |
| Receding contact angle | 40 | 50 | 39 | 42 | 44 | 51 | 42 |

TABLE 4

| | | (% by mass) | | Examples | | | | | |
|---|---|---|---|---|---|---|---|---|---|
| | | | | 8 | 9 | 10 | 11 | 12 | 13 |
| (a) | Polyalkyleneimine derivative | | (3) | | | | 0.2 | | |
| | | | (4) | | | | | 0.2 | |
| | | | (7) | | | | | | 0.2 |
| | | | (12) | 0.2 | | | | | |
| | | | (13) | | 0.2 | | | | |
| | | | (14) | | | 0.2 | | | |
| (b) | Stearyl alcohol | | | 4.5 | 4 | 4 | 4 | 4 | 4 |
| (c) | N,N-Dimethyl-3-octadecyloxypropylamine | | | 1 | 1 | 1 | 1 | 1 | 1 |
| Other | Benzyl alcohol | | | 0.5 | 0.4 | 0.4 | 0.5 | 0.5 | 0.5 |
| | Dipropylene glycol | | | 2 | | | 2 | 2 | 2 |
| | High-oleic sunflower oil | | | 0.2 | | | | | |
| | 90% Lactic acid | | | 0.6 | 0.5 | 0.5 | 0.8 | 0.8 | 0.8 |
| | Perfume | | | 0.5 | 0.5 | 0.5 | 0.5 | 0.5 | 0.5 |
| | Sodium hydroxide | | | q.s. | q.s. | q.s. | q.s. | q.s. | q.s. |
| | Water | | | bal. | bal. | bal. | bal. | bal. | bal. |
| pH (20-fold (mass) water dilute, 25° C.) | | | | 4.7 | 4.8 | 4.8 | 3.7 | 3.8 | 3.8 |
| DSC endothermic peak temp. (° C.) | | | | 68 | 69 | 69 | 67 | 68 | 67 |
| Viscosity (mPa · s) | | | | 20000 | 22000 | 16000 | 24000 | 18000 | 24000 |
| Evaluation Friction coeff. in wet state | | | | 0.20 | 0.24 | 0.41 | 0.19 | 0.24 | 0.24 |
| Receding contact angle | | | | 40 | 41 | 36 | 41 | 40 | 43 |

TABLE 5

| | | (% by mass) | | Comparative Examples | | | | |
|---|---|---|---|---|---|---|---|---|
| | | | | 1 | 2 | 3 | 4 | 5 |
| (a') | Polyalkyleneimine derivative | | (8) | 0.2 | | | | |
| | (not component (a)) | | (9) | | 0.2 | 0.2 | | |
| | | | (10) | | | | 0.2 | |
| | | | (11) | | | | | 0.2 |
| (b) | Cetyl alcohol | | | | 2 | | 2 | 2 |
| | Stearyl alcohol | | | 4 | 2 | 4 | | 2 |
| | Behenyl alcohol | | | | | | 2 | |
| (c) | N,N-Dimethyl-3-octadecyloxypropylamine | | | 1 | | 1 | | |
| | Octadecyloxy(2-hydroxypropyl)dimethylamine | | | | 1 | | | |
| | Behenylamidopropyldimethylamine | | | | | | 1 | |
| | Stearamidopropyldimethylamine | | | | | | | 1 |
| Other | Benzyl alcohol | | | 0.5 | 0.2 | 0.2 | 0.2 | 0.3 |
| | Dipropylene glycol | | | | 2 | 2 | | |
| | 90% Lactic acid | | | 0.5 | 0.8 | 0.8 | 0.7 | 0.7 |
| | Perfume | | | 0.5 | 0.5 | 0.5 | 0.5 | 0.5 |
| | Sodium hydroxide | | | q.s. | q.s. | q.s. | q.s. | q.s. |
| | Water | | | bal. | bal. | bal. | bal. | bal. |
| pH (20-fold (mass) water dilute, 25° C.) | | | | 4.8 | 4.7 | 4 | 4.6 | 4.6 |
| DSC endothermic peak temp. (° C.) | | | | 67 | 65 | 68 | 69 | 66 |
| Viscosity (mPa · s) | | | | 16000 | 12000 | 10000 | 20000 | 18000 |
| Evaluation Friction coeff. in wet state | | | | 0.64 | 0.65 | 0.7 | 0.80 | 0.61 |
| Receding contact angle | | | | 0 | 0 | 0 | 0 | 15 |

TABLE 6

|  | (% by mass) |  | Comparative Examples ||||||| 
|---|---|---|---|---|---|---|---|---|---|
|  |  |  | 6 | 7 | 8 | 9 | 10 | 11 | 12 |
| (a) | Polyalkyleneimine derivative | (1) | 0.2 |  |  |  |  |  |  |
|  |  | (2) |  | 0.2 |  |  |  |  |  |
|  |  | (4) |  |  | 0.2 |  |  |  |  |
|  |  | (5) |  |  |  | 0.2 |  |  |  |
| (b) | Stearyl alcohol |  | 1 |  |  | 5 | 5 | 5 | 5 |
|  | Behenyl alcohol |  | 3 |  |  |  |  |  |  |
| (c) | N,N-Dimethyl-3-octadecyloxypropylamine |  |  | 1 |  | 1 | 1 | 1 | 1 |
|  | Behenyltrimethylammonium chloride |  | 1 |  |  |  |  |  |  |
| Other | Polyoxyethylene(16) lauryl ether |  |  | 2 | 2 |  |  |  |  |
|  | Polydimethylsiloxane (*1) |  |  |  |  |  | 2 | 6 |  |
|  | Amino-modified silicone (*2) |  |  |  |  |  | 0.5 | 2 |  |
|  | Amino-modified silicone (*3) |  |  |  |  |  |  |  | 0.5 |
|  | Benzyl alcohol |  |  | 0.2 | 0.2 | 0.8 |  | 0.5 | 0.5 |
|  | Dipropylene glycol |  |  |  | 2 |  |  |  |  |
|  | Isopropyl palmitate |  |  |  |  | 2 |  |  |  |
|  | High-oleic sunflower oil |  |  |  |  | 2.5 |  |  |  |
|  | 90% Lactic acid |  | 1 | 0.7 | 0.8 | 0.6 | 0.5 | 0.5 | 0.7 |
|  | Perfume |  | 0.5 | 0.5 | 0.5 | 0.5 | 0.5 | 0.5 | 0.5 |
|  | Sodium hydroxide |  | q.s. | q.s. | q.s. | q.s. | q.s. | q.s. | q.s. |
|  | Water |  | bal. | bal. | bal. | bal. | bal. | bal. | bal. |
|  | pH (20-fold (mass) water dilute, 25° C.) |  | 4 | 4.6 | 4.7 | 4.7 | 4.4 | 4.4 | 4.4 |
|  | DSC endothermic peak temp. (° C.) |  | 78 | 59*4 | 61*4 | 55 | 70 | 69 | 69 |
|  | Viscosity (mPa · s) |  | 34000 | 600 | 400 | 23000 | 30000 | 13000 | 28000 |
| Evaluation | Friction coeff. in wet state |  | 0.59 | 0.68 | 0.77 | 0.72 | 0.68 | 1.02 | 0.95 |
|  | Receding contact angle |  | 0 | 0 | 0 | 0 | 5 | 35 | 10 |

(*1): KHS-3 (product of Shin-Etsu Chemical Co., Ltd.)
(*2): XS65-C0032 (product of Momentive Performance Materials Inc.)
(*3): Amino-modified silicone disclosed in Synthesis Example 1 of JP2002-308738 A
*4 Melting temperature of polymer

Example 14

Hair Conditioner (pH 3.3)

|  | (% by mass) |
|---|---|
| N,N-Dimethyl-3-octadecyloxypropylamine | 1.5 |
| Polyalkyleneimine derivative (4) | 0.4 |
| Stearyl alcohol | 6.0 |
| Dipropylene glycol | 5.0 |
| Benzyl alcohol | 0.5 |
| Methylpolysiloxane mixture liquid | 2.0 |
| Amino-modified dimethylpolysiloxane | 0.3 |
| Lactic acid | 1.0 |
| Menthol | 1.0 |
| Perfume | 0.4 |
| Sodium hydroxide | q.s. |
| Ion-exchange water | balance |

*Endothermic peak temperature in DSC: 68° C.

The above conditioner can restore intrinsic hydrophobicity of hydrophilicized hair and attain low friction of the hair, to thereby impart water repellency and low friction to the hair in a wet state. Thus, entangling of hair during styling can be prevented, and favorable hair sensation can be maintained even after drying.

Example 15

Hair Conditioner (pH 3.3)

|  | (% by mass) |
|---|---|
| N-(3-(Dimethylamino)propyl)docosanamide | 1.5 |
| Stearyl alcohol | 3.0 |
| Cetyl alcohol | 2.0 |
| Polyalkyleneimine derivative (4) | 0.2 |
| Benzyl alcohol | 0.3 |
| Glycerin | 1.0 |
| Sunflower oil | 0.2 |
| Methylpolysiloxane mixture liquid | 2.5 |
| Amino-modified polydimethylsiloxane | 0.5 |
| Lactic acid | 1.0 |
| Perfume | 0.4 |
| Sodium hydroxide | q.s. |
| Ion-exchange water | balance |

*Endothermic peak temperature in DSC: 64° C.

The above conditioner can restore intrinsic hydrophobicity of hydrophilicized hair and attain low friction of the hair, to thereby impart water repellency and low friction to the hair in a wet state. Thus, entangling of hair during styling can be prevented, and favorable hair sensation can be maintained even after drying.

Example 16

Hair Conditioner (pH 4.5)

|  | (% by mass) |
|---|---|
| N,N-Dimethyl-3-octadecyloxypropylamine | 1.5 |
| Stearyl alcohol | 5.5 |
| Polyalkyleneimine derivative (2) | 0.5 |
| Dipropylene glycol | 3.0 |
| Benzyl alcohol | 0.8 |
| Methylpolysiloxane mixture liquid | 1.5 |
| Amino-modified polydimethylsiloxane | 0.3 |
| Lactic acid | 0.8 |

| | (% by mass) |
|---|---|
| Perfume | 0.4 |
| Sodium hydroxide | q.s. |
| Ion-exchange water | balance |

*Endothermic peak temperature in DSC: 68° C.

The above conditioner can impart water repellency and low friction to hydrophilicized hair in a wet state. Thus, entangling of hair during styling can be prevented, and favorable hair sensation can be maintained even after drying.

In the above Examples, a predetermined amount of the polyalkyleneimine derivative was incorporated into the gel-form hair cosmetic composition. However, even when the polyalkyleneimine derivative content of the gel-form hair cosmetic composition is modified to, for example, from 0.05 to 10% by mass, water repellency and low friction can be imparted to hydrophilicized hair in a wet state, whereby entangling of hair during styling can be prevented, and favorable hair sensation can be maintained even after drying.

The invention claimed is:

1. A hair cosmetic composition, which is an aqueous composition comprising components (a), (b), and (c) emulsified in an aqueous component, which composition exhibits an endothermic peak temperature of 40° C. to 75° C. as measured by a differential scanning calorimeter (DSC), wherein the components (a), (b), and (c) are:
    (a) a polyalkyleneimine derivative or a salt thereof, the polyalkyleneimine derivative being formed of a polyalkyleneimine having a weight average molecular weight of 3,300 g/mol or more to 50,000 g/mol or less, in which at least one of the substituents represented by any of formulas (I), (II), and (III) is bonded to 60 mol % or more of the nitrogen atoms of the polyalkyleneimine, the formulas being:

$$R^1-CO- \quad (I)$$

$$R^2-(CH_2)_n-CHX-CH_2- \quad (II)$$

$$R^3-NH-CO- \quad (III)$$

wherein, in formula (I), $R^1$ has a linear chain or branched chain structure and is selected from the group consisting of a hydrogen atom, an alkyl group, an alkenyl group, and a hydroxyalkyl group;
    in formula (II), $R^2$ has a linear chain or branched chain structure and is selected from the group consisting of a hydrogen atom, an alkyl group, an alkoxy group, an alkenyl group, and an alkenyloxy group; n is an integer of 0 or 1; when $R^2$ is a hydrogen atom, a linear-chain or a branched-chain alkyl group, or a linear-chain or a branched-chain alkenyl group, n is 0; when $R^2$ is an alkoxy group or an alkenyloxy group, n is 1; and X represents a hydrogen atom or a hydroxyl group;
    in formula (III), $R^3$ has a linear chain or branched chain structure and is selected from the group consisting of a hydrogen atom, an alkyl group and an alkenyl group; and
    $R^1$, $R^2$, and $R^3$ may be identical to or different from one another, and at least one of $R^1$, $R^2$, and $R^3$ is a group having 13 or more carbon atoms; the entirety of $R^1$, $R^2$, and $R^3$ has an average number of carbon atoms of 9 or more; and the entirety of $R^1$, $R^2$, and $R^3$ has a linear group content of 30 mol % or more;
    (b) a C12 to C28 saturated aliphatic alcohol; and
    (c) a cationic surfactant,
    wherein a viscosity of the hair cosmetic composition is from 250 mPa·s to 100,000 mPa·s as measured with a TVB10 viscometer with a T-bar stage TS-10, and
    wherein, among groups $R^1$, $R^2$, and $R^3$, a content of groups having at least 13 carbon atoms is 70 mol % or more.

2. The hair cosmetic composition according to claim 1, wherein, in the component (a), the entirety of $R^1$, $R^2$, and $R^3$ has a linear structure content of 40 mol % or more to 90 mol % or less.

3. The hair cosmetic composition according to claim 1, wherein, in the component (a), the ratio of the number of groups represented by formula (I) to the number of all substituents is 20 mol % or more, and the ratio of the total number of groups represented by formulas (II) and (III) to the number of all substituents is 80 mol % or less.

4. The hair cosmetic composition according to claim 1, wherein the component (a) content is 0.05% by mass or more to 10.0% by mass or less with respect to the total mass of the hair cosmetic composition.

5. The hair cosmetic composition according to claim 1, wherein the component (a) content is 0.1% by mass or more to 3.0% by mass or less with respect to the total mass of the hair cosmetic composition.

6. The hair cosmetic composition according to claim 1, wherein the component (b) is a C12 to C22 saturated aliphatic alcohol.

7. The hair cosmetic composition according to claim 1, wherein the component (b) is selected from the group consisting of lauryl alcohol, myristyl alcohol, cetyl alcohol, stearyl alcohol, and behenyl alcohol.

8. The hair cosmetic composition according to claim 1, wherein the component (b) content is 0.1% by mass or more to 20% by mass or less with respect to the total mass of the hair cosmetic composition.

9. The hair cosmetic composition according to claim 1, wherein the component (b) content is 0.5% by mass or more to 15% by mass or less with respect to the total mass of the hair cosmetic composition.

10. The hair cosmetic composition according to claim 1, wherein the component (c) is selected from the group consisting of an ether amine or a salt thereof, an amide amine or a salt thereof, and a quaternary ammonium salt.

11. The hair cosmetic composition according to claim 1, wherein the component (c) content is 0.01% by mass to 20% by mass or less with respect to the total mass of the hair cosmetic composition.

12. The hair cosmetic composition according to claim 1, wherein the component (c) content is 0.1% by mass to 15% by mass or less with respect to the total mass of the hair cosmetic composition.

13. The hair cosmetic composition according to claim 1, wherein the ratio by mole of the component (b) to the component (c) is 2.0 or more to 10.0 or less.

14. The hair cosmetic composition according to claim 1, wherein the ratio by mole of the component (b) to the component (c) is 2.5 or more to 10.0 or less.

15. The hair cosmetic composition according to claim 1, wherein the total amount of any non-volatile solvent and oily agent which are liquid at ambient temperature and have a solubility parameter δ of 20 or less, if present, is 4.0% by mass or less.

16. The hair cosmetic composition according to claim 1, which has a pH of 2.0 or more to 7.5 or less at 25° C. when diluted 20-fold by mass with water.

17. A method for modifying hair, comprising applying to hair a hair cosmetic composition according to claim 1, and spreading the composition over the hair.

18. A method for modifying hair, comprising applying to hair a hair cosmetic composition according to claim 1, spreading the composition over the hair, and rinsing off the composition.

19. The hair cosmetic composition according to claim 1, wherein at least one of the substituents represented by any of formulas (I), (II), and (III) is bonded to 50 mol % or more of the nitrogen atoms of the polyalkyleneimine.

20. The hair cosmetic composition according to claim 1, wherein, among groups $R^1$, $R^2$, and $R^3$, the average number of carbon atoms per group is 12 or more.

* * * * *